United States Patent
Boualleg et al.

(10) Patent No.: US 10,307,738 B2
(45) Date of Patent: Jun. 4, 2019

(54) NICKEL-BASED MESOPOROUS CATALYST AND USE THEREOF IN HYDROGENATION

(71) Applicant: IFP Energies Nouvelles, Rueil-Malmaison (FR)

(72) Inventors: Malika Boualleg, Villeurbanne (FR); Anne-Claire Dubreuil, Lyons (FR); Emily Maille, Lyons (FR); Cecile Thomazeau, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 37 days.

(21) Appl. No.: 15/509,873

(22) PCT Filed: Aug. 21, 2015

(86) PCT No.: PCT/EP2015/069223
§ 371 (c)(1),
(2) Date: Mar. 9, 2017

(87) PCT Pub. No.: WO2016/037830
PCT Pub. Date: Mar. 17, 2016

(65) Prior Publication Data
US 2017/0259249 A1 Sep. 14, 2017

(30) Foreign Application Priority Data

Sep. 11, 2014 (FR) ...................... 14 58543

(51) Int. Cl.
| | | |
|---|---|---|
| *B01J 23/755* | (2006.01) | |
| *B01J 37/03* | (2006.01) | |
| *B01J 37/08* | (2006.01) | |
| *B01J 21/04* | (2006.01) | |
| *B01J 35/10* | (2006.01) | |
| *B01J 37/02* | (2006.01) | |
| *C01F 7/34* | (2006.01) | |
| *C07C 7/163* | (2006.01) | |
| *C10G 45/36* | (2006.01) | |
| *C10G 45/48* | (2006.01) | |
| *C01F 7/14* | (2006.01) | |
| *C01F 7/44* | (2006.01) | |
| *B01J 35/00* | (2006.01) | |
| *B01J 37/00* | (2006.01) | |

(Continued)

(52) U.S. Cl.
CPC ............. *B01J 23/755* (2013.01); *B01J 21/04* (2013.01); *B01J 35/0006* (2013.01); *B01J 35/006* (2013.01); *B01J 35/0013* (2013.01); *B01J 35/026* (2013.01); *B01J 35/10* (2013.01); *B01J 35/108* (2013.01); *B01J 35/1019* (2013.01); *B01J 35/1038* (2013.01); *B01J 35/1042* (2013.01); *B01J 35/1061* (2013.01); *B01J 37/009* (2013.01); *B01J 37/0009* (2013.01); *B01J 37/0201* (2013.01); *B01J 37/0205* (2013.01); *B01J 37/0207* (2013.01); *B01J 37/0213* (2013.01); *B01J 37/0236* (2013.01); *B01J 37/031* (2013.01); *B01J 37/035* (2013.01); *B01J 37/036* (2013.01); *B01J 37/08* (2013.01); *B01J 37/16* (2013.01); *C01F 7/141* (2013.01); *C01F 7/34* (2013.01); *C01F 7/441* (2013.01); *C07C 7/163* (2013.01); *C10G 45/36* (2013.01); *C10G 45/48* (2013.01); *B01J 23/835* (2013.01); *B01J 23/892* (2013.01); *B01J 37/18* (2013.01); *C01P 2006/12* (2013.01); *C01P 2006/14* (2013.01); *C01P 2006/16* (2013.01); *C10G 2300/705* (2013.01)

(58) Field of Classification Search
CPC ...... B01J 23/755; B01J 21/04; B01J 35/0006; B01J 35/006; B01J 35/026; B01J 35/10; B01J 35/1019; B01J 35/1038; B01J 35/1042; B01J 35/1061; B01J 35/108; C07C 7/163; C10G 45/36; C10G 45/48
USPC .................. 502/335; 585/250, 267, 270
See application file for complete search history.

(56) References Cited

U.S. PATENT DOCUMENTS

| | | | |
|---|---|---|---|
| 4,631,265 A | 12/1986 | Oudejans et al. | |
| 4,657,889 A | 4/1987 | Ganguli et al. | |

(Continued)

FOREIGN PATENT DOCUMENTS

| | | | | |
|---|---|---|---|---|
| EP | 0168091 A1 * | 1/1986 | ............ | B01J 23/755 |
| EP | 0168091 A1 | 1/1986 | | |

(Continued)

OTHER PUBLICATIONS

International Search Report dated Oct. 26, 2015 issued in corresponding PCT/EP2015/069223 application (4 pages).

*Primary Examiner* — Patricia L. Hailey
(74) *Attorney, Agent, or Firm* — Millen, White, Zelano and Branigan, P.C.

(57) ABSTRACT

A supported catalyst having a calcined, predominantly aluminum, oxide support and an active phase of 5 to 65% by weight nickel with respect to the total mass of the catalyst, said active phase having no group VIB metal, the nickel particles having a diameter less than or equal to 20 nm, said catalyst having a mesopore median diameter greater than or equal to 14 nm, a mesopore volume measured by mercury porosimetry greater than or equal to 0.45 mL/g, a total pore volume measured by mercury porosimetry greater than or equal to 0.45 mL/g, a macropore volume less than 5% of the total pore volume, said catalyst being in the form of grains having an average diameter comprised between 0.5 and 10 mm. The invention also relates to the process for the preparation of said catalyst and the use thereof in a hydrogenation process.

14 Claims, No Drawings

(51) Int. Cl.
  *B01J 35/02* (2006.01)
  *B01J 37/16* (2006.01)
  *B01J 23/835* (2006.01)
  *B01J 23/89* (2006.01)
  *B01J 37/18* (2006.01)

(56) References Cited

U.S. PATENT DOCUMENTS

| | | |
|---|---|---|
| 4,683,088 A | 7/1987 | Oudejans et al. |
| 4,734,392 A | 3/1988 | Ganguli et al. |
| 4,920,089 A * | 4/1990 | Van Beek ............... B01J 21/04 208/143 |
| 5,047,178 A | 9/1991 | Ganguli et al. |
| 5,478,791 A | 12/1995 | Baldauf et al. |
| 6,171,573 B1 | 1/2001 | Sato |
| 6,589,908 B1 | 7/2003 | Ginestra et al. |
| 8,633,131 B2 * | 1/2014 | Lee ......................... B01J 21/04 502/300 |
| 8,969,239 B2 | 3/2015 | Ginestra et al. |
| 9,790,652 B1 | 10/2017 | Kim et al. |
| 2005/0101480 A1 | 5/2005 | Ackerman et al. |
| 2010/0105546 A1 * | 4/2010 | Xu ......................... B01J 23/755 502/242 |
| 2010/0276339 A1 | 11/2010 | Ginestra et al. |
| 2013/0053237 A1 * | 2/2013 | Xu ......................... B01J 21/063 502/207 |
| 2014/0134098 A1 * | 5/2014 | Faria ..................... B01J 23/755 423/648.1 |
| 2017/0120224 A1 * | 5/2017 | Boualleg ............. B01J 35/1019 |

FOREIGN PATENT DOCUMENTS

| | | | |
|---|---|---|---|
| EP | 0885844 A1 * | 12/1998 | .............. B01J 13/00 |
| EP | 0885844 A1 | 12/1998 | |
| WO | 2005/028106 A1 | 3/2005 | |

* cited by examiner

NICKEL-BASED MESOPOROUS CATALYST AND USE THEREOF IN HYDROGENATION

FIELD OF THE INVENTION

A subject of the invention is a catalyst supported on a calcined, predominantly aluminium, oxide support with an active nickel phase having a texture and a formulation that are favourable to hydrogenation reactions, in particular to reactions of selective hydrogenation of polyunsaturated compounds or hydrogenation of aromatics. The invention also relates to the process for the preparation of said catalyst as well as the use thereof in hydrogenation reactions.

The catalysts of selective hydrogenation or hydrogenation of aromatics are generally based on metals of group VIII of the periodic table, such as nickel. The metal is presented in the form of nanometric metallic particles deposited on a support which can be a refractory oxide. The group VIII metal content, the optional presence of a second metallic element, the size of the metal particles and the distribution of the active phase in the support as well as the nature and pore distribution of the support are parameters which have a significance with respect to the performances of the catalysts.

The rate of the hydrogenation reaction is governed by several criteria, such as the diffusion of the reagents on the surface of the catalyst (external diffusional limitations), the diffusion of the reagents in the porosity of the support towards the active sites (internal diffusional limitations) and the intrinsic properties of the active phase such as the size of the metallic particles and the distribution of the active phase within the support.

As regards the size of the metallic particles, it is generally accepted that the catalyst is all the more active, the size of the particles is smaller. In addition, it is important to obtain a particle size distribution centred on the optimum value as well as a narrow distribution around this value.

As regards the internal diffusional limitations, it is important that the pore distribution of the macropores and mesopores is suitable for the desired reaction in order to ensure the diffusion of the reagents in the porosity of the support towards the active sites as well as the outward diffusion of the products formed.

Numerous developments thus relate to the optimization of the pore distribution of the catalyst by the optimization of the catalyst support.

Document WO2011/080515 describes a nickel-based hydrogenation catalyst supported on alumina having a nickel content greater than 35% by weight, said catalyst having a high dispersion of nickel (0) over the surface of an alumina with very open porosity and with a high specific surface area. The pore distribution of the support is bimodal: at least 30% of the total pore volume is constituted by pores having a diameter comprised between 5 and 20 nm, at least 20% of the total pore volume is constituted by pores having a diameter comprised between 100 and 700 nm with a total pore volume of the support of at least 1.0 mL/g. The nickel surface area must be greater than or equal to 110 $m^2$ per gram of nickel.

Document U.S. Pat. No. 6,673,743 describes an alumina-based catalyst having a nickel content between 5 and 75% by weight with a nickel surface area greater than 80 $m^2$ per gram of nickel and a median diameter greater than 10 nm, said catalyst being in the form of particles having a diameter D[3,2] between 1 and 20 µm, i.e. it is in the form of powder.

Document U.S. Pat. No. 5,478,791 describes an alumina-based catalyst having a nickel content between 10 and 60% by weight, the nickel particles having a diameter between 15 and 50 nm. The total volume of the catalyst is comprised between 0.3 and 0.75 g/L and between 15 and 75% of the total pore volume is located in pores having a diameter greater than 100 nm. The catalyst also has micropores.

Finally, document U.S. Pat. No. 4,920,089 describes an alumina-based catalyst having a nickel content between 5 and 40% by weight with a nickel surface area comprised between 80 and 300 $m^2$ per gram of nickel. The alumina has a particular XRD diffractogram. The pore distribution of the catalyst is comprised between 3.5 and 30 nm, and preferably comprised between 4 and 20 nm.

In this context, one of the objectives of the present invention is to propose a supported catalyst with an active nickel phase having hydrogenation performances, in terms of activity, at least as good as those of the catalysts known in the state of the art.

More particularly, the invention relates to a supported catalyst comprising a calcined, predominantly aluminium, oxide support and an active phase comprising nickel, the nickel content being comprised between 5 and 65% by weight of said element with respect to the total mass of the catalyst, said active phase comprising no group VIB metal, the nickel particles having a diameter less than or equal to 20 nm, said catalyst having a mesopore median diameter greater than or equal to 14 nm, a mesopore volume measured by mercury porosimetry greater than or equal to 0.45 mL/g, a total pore volume measured by mercury porosimetry greater than or equal to 0.45 mL/g, a macropore volume less than 5% of the total pore volume, said catalyst being in the form of grains having an average diameter comprised between 0.5 and 10 mm.

The applicant has discovered that a catalyst prepared by impregnation of the active phase on an alumina resulting from the calcination of a particular alumina gel prepared according to the preparation process described below, makes it possible to obtain a catalyst which has a pore distribution as well as a size of nickel particles particularly suitable for hydrogenation reactions, in particular selective hydrogenation reactions of polyunsaturated molecules such as the diolefins, acetylenics or alkenylaromatics, or for hydrogenation reactions of the aromatics.

In fact, the pore distribution resulting from the process for the preparation of the calcined aluminium oxide support originating from a specific alumina gel, makes it possible to provide a porosity that is particularly suitable for promoting the diffusion of the reagents in the porous medium, then reaction thereof with the active phase. Without being bound to any theory, it appears that the particular textural properties of the catalyst according to the invention, in particular a monomodal porosity with the presence of mesopores of a controlled size, makes it possible to obtain a catalyst having hydrogenation performances, in terms of activity, at least as good as those of the known catalysts of the state of the art. The catalyst according to the invention is characterized by a high mesopore volume with a high median diameter of the mesopores coupled with a macropore volume that is of very low value, or even absent. In fact, it is well known that although the presence of a macropore value can reduce the internal diffusional limitations, at the same time it weakens the mechanical strength of the catalyst. It is therefore important to limit the percentage of the macropore volume with respect to the total pore volume in order to obtain a catalyst having the sought catalytic performances and a sufficient mechanical strength. In addition, the presence of a high total pore volume of the catalyst according to the invention makes it possible to impregnate a high active phase content in a single pass.

According to a variant, the mesopore median diameter is comprised between 18 and 25 nm.

According to a variant, the mesopore volume of the catalyst is comprised between 0.55 mL/g and 0.95 mL/g.

According to a variant, the macropore volume of the catalyst is less than 3.5% of the total pore volume.

According to a variant, the nickel content is comprised between 10 and 34% by weight of said element with respect to the total mass of the catalyst.

According to a variant, the catalyst contains no pores between 2 and 7 nm. According to a variant, the catalyst contains no micropores.

The invention also relates to the process for the preparation of said catalyst. The invention also relates to the use of the catalyst in a hydrogenation process in which the catalyst according to the invention, or capable of being prepared according to the preparation process according to the invention is brought into contact, in the presence of hydrogen, with a feedstock of hydrocarbons containing polyunsaturated and/or aromatic molecules so as to obtain an at least partially hydrogenated effluent.

DETAILED DESCRIPTION

The Catalyst According to the Invention

The catalyst according to the invention is presented in the form of a supported catalyst comprising a calcined, predominantly aluminium, oxide support and an active phase comprising nickel. The characteristics of the alumina gel that led to the production of the alumina, predominantly contained in said support, as well as the textural properties obtained with the active phase, give the catalyst according to the invention its specific properties.

More particularly, the invention relates to a supported catalyst comprising a calcined, predominantly aluminium, oxide support and an active phase comprising nickel, the nickel content being comprised between 5 and 65% by weight of said element with respect to the total mass of the catalyst, said active phase comprising no group VIB metal, the nickel particles having a diameter less than or equal to 20 nm, said catalyst having a mesopore median diameter greater than or equal to 14 nm, a mesopore volume measured by mercury porosimetry greater than or equal to 0.45 mL/g, a total pore volume measured by mercury porosimetry greater than or equal to 0.45 mL/g, a macropore volume less than 5% of the total pore volume, said catalyst being in the form of grains having an average diameter comprised between 0.5 and 10 mm.

The catalyst according to the invention and the support used for the preparation of the catalyst according to the invention have particular textural properties, in particular a specific pore distribution, where the macropore and mesopore volumes are measured by mercury intrusion and the micropore volume is measured by nitrogen adsorption.

By "macropores" is meant pores the opening of which is greater than 50 nm.

By "mesopores" is meant pores the opening of which is comprised between 2 nm and 50 nm inclusive.

By "micropores" is meant pores the opening of which is less than 2 nm.

By total pore volume of the catalyst or of the support used for the preparation of the catalyst according to the invention is meant the volume measured with a mercury intrusion porosimeter according to standard ASTM D4284-83 at a maximum pressure of 4000 bar (400 MPa), using a surface tension of 484 dyne/cm and a contact angle of 140°. The wetting angle was taken to be equal to 140° following the recommendations in the work "Techniques de l'ingénieur, traité analyse and caractérisation" (Techniques of the engineer, a treatise on analysis and characterization), pages 1050-1055, written by Jean Charpin and Bernard Rasneur.

In order to obtain greater accuracy, the value of the total pore volume corresponds to the value of the total pore volume measured with a mercury intrusion porosimeter measured on the sample, minus the value of the total pore volume measured with a mercury intrusion porosimeter measured on the same sample for a pressure corresponding to 30 psi (approximately 0.2 MPa).

The volume of the macropores and mesopores is measured by mercury intrusion porosimetry according to standard ASTM D4284-83 at a maximum pressure of 4000 bar (400 MPa), using a surface tension of 484 dyne/cm and a contact angle of 140°. The value starting from which the mercury fills all the intergranular voids is fixed at 0.2 MPa, and it is considered that beyond this, the mercury penetrates into the pores of the sample.

The macropore volume of the catalyst or of the support used for the preparation of the catalyst according to the invention is defined as being the cumulative volume of mercury introduced at a pressure comprised between 0.2 MPa and 30 MPa, corresponding to the volume contained in the pores with an apparent diameter greater than 50 nm.

The mesopore volume of the catalyst or of the support used for the preparation of the catalyst according to the invention is defined as the cumulative volume of mercury introduced at a pressure comprised between 30 MPa and 400 MPa, corresponding to the volume contained in the pores with an apparent diameter comprised between 2 and 50 nm.

The volume of the micropores is measured by nitrogen porosimetry. Quantitative analysis of the microporosity is carried out on the basis of the "t" method (method of Lippens-De Boer, 1965), which corresponds to a transform of the initial adsorption isotherm as described in the work "Adsorption by powders and porous solids. Principles, methodology and applications" written by F. Rouquérol, J. Rouquérol and K. Sing, Academic Press, 1999.

The mesopore median diameter is also defined as being the diameter such that all the pores, among all of the pores constituting the mesopore volume, smaller than this diameter constitute 50% of the total mesopore volume determined with a mercury intrusion porosimeter.

The median macropore diameter is also defined as being the diameter such that all the pores, among all of the pores constituting the macropore volume, smaller than this diameter constitute 50% of the total macropore volume determined with a mercury intrusion porosimeter.

By specific surface area of the catalyst or of the support used for the preparation of the catalyst according to the invention is meant the BET specific surface area determined by nitrogen adsorption according to standard ASTM D 3663-78 based on the BRUNAUER-EMMETT-TELLER method described in the periodical "The Journal of the American Chemical Society", 60, 309, (1938).

Hereinafter, the groups of chemical elements are given according to the CAS classification (CRC Handbook of Chemistry and Physics, publisher CRC Press, editor in chief D. R. Lide, 81st edition, 2000-2001). For example, group VIII according to the CAS classification corresponds to the metals of columns 8, 9 and 10 according to the new IUPAC classification.

Characteristics of the Support According to the Invention

The support of the catalyst according to the invention comprises predominantly a calcined porous aluminium oxide.

Said support has an alumina content greater than or equal to 90% by weight with respect to the weight of said support, optionally supplemented by silica and/or phosphorus at a total content of at most 10% by weight in $SiO_2$ and/or $P_2O_5$, equivalent, preferably less than 5% by weight, and very preferably less than 2% by weight with respect to the total weight of said matrix. The silica and/or the phosphorus can be introduced, by any technique known to a person skilled in the art, during synthesis of the alumina gel or by impregnation of the support used for the preparation of the catalyst according to the invention.

Even more preferably, the calcined, predominantly alumina, porous oxide support is constituted by alumina.

Preferably, the alumina present in said support is a transition alumina such as a gamma-, delta-, theta-, chi-, rho- or eta-alumina, alone or in a mixture. More preferably, the alumina is a gamma-, delta- or theta-transition alumina, alone or in a mixture.

The following characteristics of the support correspond to the characteristics of the support used for the preparation of the catalyst according to the invention before impregnation of the active phase.

The support used for the preparation of the catalyst according to the invention advantageously has a total pore volume greater than or equal to 0.68 ml/g, preferably greater than or equal to 0.70 ml/g, and particularly preferably comprised between 0.70 and 1.0 ml/g.

The support used for the preparation of the catalyst according to the invention advantageously has a macropore volume less than 5% of the total pore volume of the support, preferably less than 3.5% of the total pore volume of the support. According to a variant, the support used for the preparation of the catalyst according to the invention has a macropore volume less than 0.05 mL/g.

The mesopore volume of the support used for the preparation of the catalyst according to the invention is greater than or equal to 0.68 ml/g, preferably greater than or equal to 0.70 ml/g, and particularly preferably comprised between 0.70 and 1.0 ml/g.

The support used for the preparation of the catalyst according to the invention has no pores with a diameter comprised between 2 and 7 nm.

The mesopore median diameter of the support used for the preparation of the catalyst according to the invention is greater than or equal to 16 nm, preferably greater than or equal to 18 nm, and particularly preferably comprised between 20 and 25 nm.

When macropores are present, the macropore median diameter of the support is advantageously comprised between 60 and 200 nm, preferably between 60 and 120 nm.

The support used for the preparation of the catalyst according to the invention has a BET specific surface area of at least 40 $m^2/g$, preferably of at least 50 $m^2/g$ and even more preferably comprised between 60 and 400 $m^2/g$.

When it is desired to use the catalyst according to the invention in a selective hydrogenation reaction of polyunsaturated molecules such as the diolefins, acetylenics or alkenylaromatics, the support used for the preparation of the catalyst according to the invention advantageously has a BET specific surface area comprised between 60 and 230 $m^2/g$.

When it is desired to use the catalyst according to the invention in a selective hydrogenation reaction of aromatics, the support used for the preparation of the catalyst according to the invention advantageously has a BET specific surface area comprised between 130 and 400 $m^2/g$.

Preferably, the support used for the preparation of the catalyst according to the invention has a low microporosity, very preferably it has no microporosity.

Characteristics of the Catalyst

The finished catalyst, i.e. with the active phase deposited on the support by any method known to a person skilled in the art, as is described below, consequently has the following textural properties.

The catalyst according to the invention has a total pore volume greater than or equal to 0.45 ml/g, preferably greater than or equal to 0.48 ml/g, and particularly preferably comprised between 0.55 and 0.95 ml/g.

The catalyst according to the invention advantageously has a macropore volume less than 5% of the total pore volume of the catalyst, preferably less than 3.5 of the total pore volume of the catalyst. According to a variant, the catalyst according to the invention has a macropore volume less than 0.05 mL/g.

The mesopore volume of the catalyst is greater than or equal to 0.45 ml/g, preferably greater than or equal to 0.48 ml/g, and particularly preferably comprised between 0.55 and 0.95 ml/g.

The catalyst according to the invention has no pores with a diameter comprised between 2 and 7 nm.

The mesopore median diameter of the catalyst is greater than or equal to 14 nm, preferably greater than or equal to 16 nm, and particularly preferably comprised between 18 and 25 nm.

When macropores are present, the macropore median diameter of the catalyst is advantageously comprised between 60 and 200 nm, preferably between 60 and 120 nm.

The catalyst according to the present invention has a BET specific surface area of at least 40 $m^2/g$, preferably of at least 50 $m^2/g$ and even more preferably comprised between 55 and 250 $m^2/g$.

When it is desired to use the catalyst according to the invention in a selective hydrogenation reaction of polyunsaturated molecules such as the diolefins, acetylenics or alkenylaromatics, the catalyst according to the invention advantageously has a BET specific surface area comprised between 55 and 170 $m^2/g$.

When it is desired to use the catalyst according to the invention in a hydrogenation reaction of aromatics, the catalyst according to the invention advantageously has a BET specific surface area comprised between 90 and 250 $m^2/g$.

Preferably, the catalyst has a low microporosity, and very preferably it has no microporosity.

The nickel content is comprised between 5 and 65% of said element with respect to the total mass of the catalyst, preferably comprised between 8 and 55% by weight, even more preferably comprised between 10 and 40% by weight, and particularly preferably comprised between 10 and 34% by weight. The Ni content is measured by X-ray fluorescence.

When it is desired to use the catalyst according to the invention in a selective hydrogenation reaction of polyunsaturated molecules such as the diolefins, the acetylenics or the alkenylaromatics, the nickel content is advantageously comprised between 5 and 25% by weight, preferably comprised between 8 and 25% by weight, and more preferentially comprised between 10 and 23% by weight of said element with respect to the total mass of the catalyst.

When it is desired to use the catalyst according to the invention in a selective hydrogenation reaction of aromatics, the nickel content is advantageously comprised between 15 and 65% by weight, preferably comprised between 18 and 55% by weight, and more preferentially comprised between 19 and 34% by weight of said element with respect to the total mass of the catalyst.

The size of the nickel particles in the catalyst according to the invention is less than 20 nm, preferably comprised between 1.5 and 18 nm. By "size of the nickel particles" is meant the diameter of the nickel crystallites in oxide form. The diameter of the nickel crystallites in oxide form is determined by X-ray diffraction, based on the width of the X-ray diffraction line situated at the 2-theta angle=43° (i.e. in the [200] crystallographic direction) using the Scherrer equation. This method, used in X-ray diffraction on powders or polycrystalline samples, that relates the half-height width of the diffraction peaks to the size of the particles, is described in detail in the reference: Appl. Cryst. (1978), 11, 102-113 "Scherrer after sixty years: A survey and some new results in the determination of crystallite size", J. I. Langford and A. J. C. Wilson.

The active phase of the catalyst can also comprise at least one additional metal selected from the group VIII metals, the group IB metals and/or tin. Preferably, the additional group VIII metal is selected from platinum, ruthenium, rhodium, as well as palladium. Advantageously, the additional group IB metal is selected from copper, gold and silver. Said additional group VIII and/or group IB metal(s) is(are) preferentially present in a content representing from 0.01 to 20% by weight of the mass of the catalyst, preferably from 0.05 to 10% by weight of the mass of the catalyst and even more preferably from 0.05 to 5% by weight of the mass of said catalyst. Tin is preferentially present in a content representing from 0.02 to 15% by weight of the mass of the catalyst, such that the Sn/Ni molar ratio is comprised between 0.01 and 0.2, preferably from 0.025 to 0.055 and even more preferably between 0.03 and 0.05.

The active phase of the catalyst comprises no group VIB metal. In particular, it comprises no molybdenum or tungsten.

Said catalyst according to the invention is in the form of grains having an average diameter comprised between 0.5 and 10 mm. The grains can have all the forms known to a person skilled in the art, for example the form of beads (preferably having a diameter comprised between 1 and 6 mm), extrudates, tablets, hollow cylinders. Preferably, the catalyst (and the support used for the preparation of the catalyst) are in the form of extrudates with an average diameter comprised between 0.5 and 10 mm, preferably between 0.8 and 3.2 mm and very preferably between 1.0 and 2.5 mm and with an average length comprised between 0.5 and 20 mm. By "average diameter" of the extrudates is meant the average diameter of the circle circumscribed by the cross-section of these extrudates. The catalyst can advantageously be in the form of cylindrical, multilobed, trilobed or tetralobed extrudates. Preferably, its form will be trilobed or tetralobed. The form of the lobes can be adjusted by all the methods known from the prior art.

Preparation Process

Another subject of the present invention is a process for the preparation of said catalyst according to the invention.

The catalyst according to the invention is prepared from a specific alumina gel. The particular pore distribution observed in the catalyst is in particular due to the preparation process based on the specific alumina gel The process for the preparation of alumina gel comprises a first precipitation step, a heating step, a second precipitation step and a filtration step. The gel is then subjected to a drying step in order to obtain a powder. The powder is then formed, then subjected to a heat treatment in order to obtain a calcined alumina porous oxide support. The calcined alumina porous oxide support is then impregnated with a solution comprising the salt(s) of the precursor(s) of the active phase, then dried in order to obtain a dried catalyst. Then the dried catalyst is optionally subjected to a heat treatment, then generally reduced and subjected to a passivation treatment.

More particularly, the preparation process for the catalyst according to the invention comprises the following steps:

a) a first step of precipitation, in an aqueous reaction medium, of at least one basic precursor selected from sodium aluminate, potassium aluminate, ammonium hydroxide, sodium hydroxide and potassium hydroxide and of at least one acidic precursor selected from aluminium sulphate, aluminium chloride, aluminium nitrate, sulphuric acid, hydrochloric acid and nitric acid, in which at least one of the basic or acidic precursors comprises aluminium, the relative flow rate of the acidic and basic precursors is selected so as to obtain a pH of the reaction medium comprised between 8.5 and 10.5 and the flow rate of the acidic and basic precursor(s) containing aluminium is adjusted so as to obtain a degree of progression of the first step comprised between 5 and 13%, the degree of progression being defined as the proportion of alumina formed in $Al_2O_3$ equivalent during said first step of precipitation with respect to the total quantity of alumina formed in $Al_2O_3$ equivalent at the end of step c) of the preparation process, said step taking place at a temperature comprised between 20 and 90° C. and for a duration comprised between 2 and 30 minutes;

b) a step of heating the suspension obtained in step a) at a temperature comprised between 40 and 90° C. for a duration comprised between 7 and 45 minutes in order to obtain an alumina gel, c) a second step of precipitation of the suspension obtained at the end of heating step b) by adding, to the suspension, at least one basic precursor selected from sodium aluminate, potassium aluminate, ammonium hydroxide, sodium hydroxide and potassium hydroxide and at least one acidic precursor selected from aluminium sulphate, aluminium chloride, aluminium nitrate, sulphuric acid, hydrochloric acid and nitric acid, in which at least one of the basic or acidic precursors comprises aluminium, the relative flow rate of the acidic and basic precursors is selected so as to obtain a pH of the reaction medium comprised between 8.5 and 10.5 and the flow rate of the acidic and basic precursor(s) containing aluminium is adjusted so as to obtain a degree of progression of the second step comprised between 87 and 95%, the degree of progression being defined as the proportion of alumina formed in $Al_2O_3$ equivalent during said second precipitation step with respect to the total quantity of alumina formed in $Al_2O_3$ equivalent at the end of step c) of the preparation process, said step taking place at a temperature comprised between 40 and 90° C. and for a duration comprised between 2 and 50 minutes;

d) a step of filtration of the suspension obtained at the end of second precipitation step c) in order to obtain an alumina gel, e) a step of drying said alumina gel obtained in step d) in order to obtain a powder, f) a step of forming the powder obtained at the end of step e) in order to obtain a crude material, g) a step of heat treatment of the crude material obtained at the end of step f) at a temperature comprised between 500 and 1000° C., in the presence or absence of an air flow containing up to 60% by volume of water, in order to obtain a calcined aluminium oxide support;

h) a step of impregnation of said support with a solution comprising the salt(s) of the precursor(s) of the nickel-based active phase i) a step of drying said impregnated support at a temperature comprised between 15 and 250° C. so as to obtain a dried catalyst, j) optionally a heat treatment of said dried catalyst at a temperature comprised between 250 and 1000° C., in the presence or absence of water.

Step a): First Precipitation

This step consists of bringing into contact, in an aqueous reaction medium, at least one basic precursor selected from sodium aluminate, potassium aluminate, ammonium hydroxide, sodium hydroxide and potassium hydroxide and at least one acidic precursor selected from aluminium sulphate, aluminium chloride, aluminium nitrate, sulphuric acid, hydrochloric acid, and nitric acid, in which at least one of the basic or acidic precursors comprises aluminium, the relative flow rate of the acidic and basic precursors is selected so as to obtain a pH of the reaction medium comprised between 8.5 and 10.5 and the flow rate of the acidic and basic precursor(s) containing aluminium is adjusted so as to obtain a degree of progression of the first step comprised between 5 and 13%, the degree of progression being defined as the proportion of alumina formed in $Al_2O_3$ equivalent during said first precipitation step with respect to the total quantity of alumina formed in $Al_2O_3$ equivalent at the end of step c) of the preparation process, said step taking place at a temperature comprised between 20 and 90° C., and for a duration comprised between 2 and 30 minutes.

Mixing at least one basic precursor and at least one acidic precursor in the aqueous reaction medium requires that at least one of the acidic or basic precursors comprises aluminium. It is also possible that at least two of the basic and acidic precursors comprise aluminium.

The basic precursors comprising aluminium are sodium aluminate and potassium aluminate. The preferred basic precursor is sodium aluminate.

The acidic precursors comprising aluminium are aluminium sulphate, aluminium chloride and aluminium nitrate. The preferred acidic precursor is aluminium sulphate.

According to the invention, the acidic alumina precursors and the basic alumina precursors can be used alone or in a mixture in the precipitation step.

Preferably, the basic and acidic precursor(s) are added in said first precipitation step a) in aqueous solution. Preferably, the aqueous reaction medium is water. Preferably, said step a) is carried out under stirring. Preferably, said step a) is carried out in the absence of organic additives.

According to the invention, the relative flow rate of the acidic and basic precursors, whether or not they contain aluminium, is selected so as to obtain a pH of the reaction medium comprised between 8.5 and 10.5, preferably comprised between 8.5 and 10, and very preferably comprised between 8.7 and 9.9.

In the preferred case where the basic and acidic precursors are respectively sodium aluminate and aluminium sulphate, the mass ratio of said basic precursor to said acidic precursor is advantageously comprised between 1.60 and 2.05.

For the other basic and acidic precursors, whether or not they contain aluminium, the base/acid mass ratios are established from a curve of neutralization of the base by the acid. Such a curve is easily obtained by a person skilled in the art.

The first precipitation step a) is carried out at a temperature comprised between 20 and 90° C., preferably between 20 and 70° C. and more preferably between 30 and 50° C.

The first precipitation step a) is carried out for a duration comprised between 2 and 30 minutes, preferably comprised between 5 and 20 minutes, and particularly preferably between 5 and 15 minutes.

According to the invention, the degree of progression of said first precipitation step a) is comprised between 5 and 13%, preferably between 6 and 12% and very preferably between 7 and 11%. The degree of progression for each of the precipitation steps is defined as the proportion of alumina formed in $Al_2O_3$ equivalent during said first or second precipitation step with respect to the total quantity of alumina formed in $Al_2O_3$ equivalent at the end of the two precipitation steps and more generally at the end of the preparation steps of the alumina gel and in particular at the end of step c) of the preparation process according to the invention.

The acidic and basic precursors containing aluminium are therefore introduced in quantities making it possible to obtain a suspension containing the desired quantity of alumina, as a function of the final concentration of alumina to be achieved.

Step b): Heating

According to the invention, said preparation process comprises a step b) of heating the suspension obtained in step a) at a temperature comprised between 40 and 90° C. for a duration comprised between 7 and 45 minutes in order to obtain an alumina gel.

Said step of heating the suspension obtained at the end of step a), implemented between said first precipitation step a) and second precipitation step c), is carried out at a temperature comprised between 40 and 90° C., preferably between 40 and 80° C., very preferably between 40 and 70° C.

Said heating step is carried out for a duration comprised between 7 and 45 minutes and preferably between 7 and 35 minutes.

Said heating step is advantageously carried out according to any methods of heating known to a person skilled in the art.

Step c): Second Precipitation

According to the invention, said preparation process comprises a second step of precipitation of the heated suspension obtained at the end of heating step b), said second step being carried out by adding, to said suspension of an aqueous solution, at least one basic precursor selected from sodium aluminate, potassium aluminate, ammonium hydroxide, sodium hydroxide and potassium hydroxide and at least one acidic precursor selected from aluminium sulphate, aluminium chloride, aluminium nitrate, sulphuric acid, hydrochloric acid, and nitric acid, in which at least one of the basic or acidic precursors comprises aluminium, the relative flow rate of the acidic and basic precursors is selected so as to obtain a pH of the reaction medium comprised between 8.5 and 10.5 and the flow rate of the acidic and basic precursor(s) containing aluminium is adjusted so as to obtain a degree of progression of the second step comprised between 87 and 95%, the degree of progression being defined as the proportion of alumina formed in $Al_2O_3$ equivalent during said second precipitation step with respect to the total quantity of alumina formed in $Al_2O_3$ equivalent at the end of step c) of the preparation process, said step being carried out at a temperature comprised between 40 and 90° C., and for a duration comprised between 2 and 50 minutes.

Just as in first precipitation step a), the addition of at least one basic precursor and of at least one acidic precursor to the heated suspension requires that at least one of the basic or acidic precursors comprises aluminium. It is also possible that at least two of the basic and acidic precursors comprise aluminium.

The basic precursors comprising aluminium are sodium aluminate and potassium aluminate. The preferred basic precursor is sodium aluminate.

The acidic precursors comprising aluminium are aluminium sulphate, aluminium chloride and aluminium nitrate. The preferred acidic precursor is aluminium sulphate.

Preferably, the basic and acidic precursor(s) are added in said step c) in aqueous solution. Preferably, the aqueous reaction medium is water. Preferably, said step c) is carried out under stirring. Preferably, said step c) is carried out in the absence of organic additives.

Just as in precipitation step a), the relative flow rate of the acidic and basic precursors, whether or not they contain aluminium, is selected so as to obtain a pH of the reaction medium comprised between 8.5 and 10.5, preferably comprised between 8.5 and 10, even more preferably comprised between 8.7 and 9.9.

In the preferred case where the basic and acidic precursors are respectively sodium aluminate and aluminium sulphate, the mass ratio of said basic precursor to said acidic precursor is advantageously comprised between 1.60 and 2.05.

For the other basic and acidic precursors, whether or not they contain aluminium, the base/acid mass ratios are established from a curve of neutralization of the base by the acid. Such a curve is easily obtained by a person skilled in the art.

The second precipitation step is carried out at a temperature comprised between 40 and 90° C., preferably comprised between 40 and 80° C., preferably between 45 and 70° C. and very preferably between 50 and 70° C.

The second precipitation step is carried out for a duration comprised between 2 and 50 minutes, preferably comprised between 5 and 45 minutes, and preferably between 7 and 40 minutes.

The aluminium precursors are also mixed in quantities making it possible to obtain a suspension containing the desired quantity of alumina, as a function of the final concentration of alumina to be achieved. In particular, said second precipitation step makes it possible to obtain 87 to 95% by weight of alumina with respect to the total quantity of alumina formed at the end of the two precipitation steps.

Just as in precipitation step a), it is the flow rate of the acidic and basic precursor(s) containing aluminium that is controlled so as to obtain a degree of progression of the second step comprised between 87 and 95%, preferably between 88 and 94%, very preferably between 89 and 93%. The degree of progression for each of the precipitation steps is defined as the proportion of alumina formed in $Al_2O_3$ equivalent during said first or second precipitation step with respect to the total quantity of alumina formed in $Al_2O_3$ equivalent at the end of the two precipitation steps and more generally at the end of the preparation steps of the alumina gel and in particular at the end of step c) of the preparation process according to the invention.

Thus, depending on the concentration of alumina required at the end of the two precipitation steps a) and c), generally comprised between 20 and 100 g/L, preferably between 20 and 80 g/L, preferably between 20 and 50 g/L, the quantities of aluminium that have to be supplied by the acidic and/or basic precursors are calculated and the flow rate of the precursors is adjusted as a function of the concentration of said aluminium precursors that are added, of the quantity of water added to the reaction medium and of the degree of progression required for each of the precipitation steps.

Just as in precipitation step a), the flow rates of the acidic and/or basic precursor(s) containing aluminium depend on the size of the reactor used and thus on the quantity of water added to the reaction medium.

By way of example, if when working in a 3 L reactor, 1 L of alumina suspension with a final $Al_2O_3$ concentration of 50 g/L is sought, with a targeted degree of progression of 10% for the first precipitation step, 10% of the total alumina must be supplied during precipitation step a). The alumina precursors are sodium aluminate at an $Al_2O_3$ concentration of 155 g/L and aluminium sulphate at an $Al_2O_3$ concentration of 102 g/L. The pH of precipitation in the first step is set at 9.5 and in the second at 9. The quantity of water added to the reactor is 620 mL.

For first precipitation step a) carried out at 30° C. for 8 minutes, the flow rate of aluminium sulphate must be 2.1 mL/min and the flow rate of sodium aluminate is 2.6 mL/min. The mass ratio of sodium aluminate to aluminium sulphate is therefore 1.91.

For the second precipitation step, carried out at 70° C., for 30 minutes, the flow rate of aluminium sulphate must be 5.2 mL/min and the flow rate of sodium aluminate is 6.3 mL/min. The mass ratio of sodium aluminate to aluminium sulphate is therefore 1.84.

Step d) Filtration

The preparation process for alumina according to the invention also comprises a step of filtration of the suspension obtained at the end of second precipitation step c) so as to obtain an alumina gel. Said filtration step is carried out by the methods known to a person skilled in the art.

Said filtration step is advantageously followed by at least one washing step, preferably with water, and preferably by one to three washing steps, with a quantity of water equal to the quantity of precipitate filtered.

The filterability of the suspension obtained at the end of the two precipitation steps is improved by the low dispersibility of the alumina gel obtained, which makes it possible to improve the productivity of the process according to the invention as well as allowing extrapolation of the process to the industrial level. Dispersibility is defined as the weight of peptized alumina solid or gel that cannot be dispersed by centrifugation in a polypropylene tube at 3600 g for 3 minutes.

At the end of the filtration step d) an alumina gel, also called boehmite, is obtained having a degree of dispersibility less than or equal to 15%, preferably comprised between 5 and 15%, and more preferably comprised between 6 and 14%, and very preferably comprised between 7 and 13%, and even more preferably comprised between 7 and 10% and a boehmite particle size comprised between 1 and 35 nm and preferably comprised between 2 and 35 nm.

The low degree of dispersibility of the gel thus prepared can facilitate the step of forming said gel by all the methods known to a person skilled in the art and in particular by mixing-extrusion, by granulation, by pelletization and by the so-called oil drop technique.

Step e) Drying the Alumina Gel

According to the invention, the alumina gel obtained at the end of second precipitation step c), followed by a filtration step d), is dried in a drying step e) in order to obtain a powder. Said drying step is generally implemented by drying at a temperature comprised between 20 and 200° C. and for a duration comprised between 8 and 15 hours, or by spray-drying or by any other drying technique known to a person skilled in the art.

In the case when said drying step e) is carried out by spray-drying, the "cake" obtained at the end of the second precipitation step, followed by a filtration step, is resuspended. Said suspension is then atomized into fine droplets, in a vertical cylindrical chamber in contact with a flow of hot air in order to evaporate the water in accordance with the principle that is well known to a person skilled in the art. The powder obtained is entrained by the heat flow to a cyclone or a bag filter, which will separate the air from the powder.

Preferably, in the case where said drying step e) is implemented by spray-drying, the spray-drying is carried out according to the operating procedure described in the publication Asep Bayu Dani Nandiyanto, Kikuo Okuyama, Advanced Powder Technology, 22, 1-19, 2011.

Step f) Forming

According to the invention, the powder obtained at the end of the drying step e) is formed in a step f) in order to obtain a crude material. By "crude material" is meant the material that has been formed and has not undergone steps of heat treatment.

Preferably, said forming step f) is carried out by any technique known to a person skilled in the art, for example the methods of forming by extrusion, by pelletizing, by the oil drop method, or by granulation on a rotating plate.

Very preferably, said forming step f) is carried out by extrusion. It is possible to use a ram extruder through a die of the desired diameter, typically between 0.5 and 10 mm.

The extrudates generally have an average diameter comprised between 0.5 and 10 mm, preferably between 0.8 and 3.2 mm and very preferably between 1.0 and 2.5 mm and an average length comprised between 0.5 and 20 mm. The extrudates can advantageously be presented in the form of cylindrical, multilobed, trilobed or tetralobed extrudates. Preferably, the form will be trilobed or tetralobed.

Any other element, for example silica in the form of a solution or an emulsion of a silicic precursor, can be introduced during the forming.

Step g) Heat Treatment

According to the invention, the crude material obtained at the end of forming step f) then undergoes a heat treatment step g) at a temperature comprised between 500 and 1000° C., in the presence or absence of an air flow containing up to 60% by volume of water.

Preferably, said heat treatment step g) is carried out at a temperature comprised between 540° C. and 850° C. Preferably, said heat treatment step g) is carried out for a duration comprised between 2 and 10 hours. The heat treatment step can be preceded by drying at a temperature comprised between 50° C. and 200° C., according to any technique known to a person skilled in the art.

By "heat treatment" is meant treatment at a temperature in the absence or in the presence of water respectively. In the latter case, contact with steam can take place at atmospheric pressure (steaming) or at autogenous pressure (autoclaving). Several combined cycles in the presence or in the absence of water can be carried out. In the case of the presence of water, the water content is preferably comprised between 150 and 900 grams per kilogram of dry air, and even more preferably between 250 and 650 grams per kilogram of dry air.

Said heat treatment step g) allows transition of the alumina gel, also called boehmite, to a calcined alumina. The alumina has a crystallographic structure of the gamma-, delta-, theta-, chi-, rho- or eta-transition alumina type, alone or in a mixture. More preferably, the alumina is a gamma-, delta- or theta-transition alumina, alone or in a mixture. The existence of the different crystallographic structures is linked to the conditions of implementation of heat treatment step g).

Step h) Impregnation of the Active Phase

According to step h) of the process according to the invention. the calcined alumina porous support is impregnated with a solution comprising the salt(s) of the precursor(s) of the nickel-based active phase.

The active phase is supplied by one or more solutions containing at least nickel. Said solution(s) can be aqueous or constituted by an organic solvent or by a mixture of water and at least one organic solvent (for example ethanol or toluene). Preferably, the solution is aqueous. The pH of this solution can be modified by the optional addition of an acid. According to another preferred variant, the aqueous solution can contain ammonium hydroxide or ammonium ions $NH_4^+$.

Preferably, said nickel precursor is introduced in aqueous solution, for example in the form of nitrate, carbonate, acetate, chloride, hydroxide, hydroxycarbonate, oxalate, complexes formed by a polyacid or an acid-alcohol and the salts thereof, complexes formed with the acetylacetonates, or any other inorganic derivative that is soluble in aqueous solution, which is brought into contact with said calcined alumina porous oxide. Preferably, nickel nitrate, nickel chloride, nickel acetate or nickel hydroxycarbonate are advantageously used as nickel precursor. Very preferably, the nickel precursor is nickel nitrate or nickel hydroxycarbonate.

According to another preferred variant, said nickel precursor is introduced in ammoniacal solution by introducing a nickel salt, for example nickel hydroxide or nickel carbonate, into an ammoniacal solution or into a solution of ammonium carbonate or ammonium hydroxide.

The quantities of the nickel precursor(s) introduced into the solution are selected so that the total nickel content is comprised between 5 and 65% by weight, preferably comprised between 8 and 55% by weight, preferably comprised between 10 and 40% by weight, and particularly preferably comprised between 10 and 34% by weight of said element with respect to the total mass of the catalyst. The nickel contents are generally suitable for the required hydrogenation reaction as described above in the paragraph of the description of the catalyst.

Any other additional element can be introduced at the time of this step: When it is desired to introduce phosphorus, a solution of phosphoric acid can be introduced into the impregnation solution.

When it is desired to introduce an additional metal selected from the group VIII metals, the group IB metals and/or tin, a salt selected from the nitrate, sulphate, chloride or any other conventional precursor can advantageously be used as precursor.

An additive, for example a chelating agent of an organic nature, can advantageously be added to the solution if this is deemed necessary by a person skilled in the art.

The impregnation of the active phase can be carried out according to all the methods known to a person skilled in the art, in particular by dry impregnation. Preferably, the nickel and optionally at least one additional element such as an additional metal selected from the group VIII metals, the group IB metals and/or tin, phosphorus or an additive such as a chelating agent of organic nature are deposited by dry impregnation of their associated precursors on the oxide support according to the invention.

Deposition can be carried out in a single step of dry impregnation of the oxide support according to the invention using a solution containing, simultaneously, at least one nickel compound, and optionally at least one additional element.

Deposition can also advantageously be carried out in at least two cycles of dry impregnation. The various elements can thus advantageously be impregnated successively or one of the elements can also be impregnated in several sequences. One of the impregnations which is carried out can in particular make it possible to introduce an organic compound in addition to the active phase of the catalyst. In these cases, each impregnation is advantageously followed by drying and optionally a heat treatment. The drying can be carried out at a temperature comprised between 15 and 250° C., preferably between 80 and 200° C., generally for a duration comprised between 10 minutes and 24 hours. The heat treatment can be carried out at a temperature comprised between 200 and 1000° C., preferentially between 250 and 750° C., generally for a duration comprised between 15 minutes and 10 hours.

Step i) Drying the Impregnated Support

According to the invention, the impregnated support obtained at the end of step h) of impregnation of the active phase undergoes a drying step i) at a temperature comprised between 15 and less than 250° C., preferably between 80 and 200° C. by any technique known to a person skilled in the art, for a duration typically comprised between 10 minutes and 24 hours. A dried catalyst is obtained.

Step j): Heat Treatment of the Dried Catalyst

The catalyst thus dried can then undergo a supplementary step of heat treatment j) at a temperature comprised between 250 and 1000° C., and preferably between 250 and 750° C. for a duration typically comprised between 15 minutes and 10 hours, in the presence or absence of water.

By "heat treatment" is meant treatment at a temperature in the absence or in the presence of water respectively. In the latter case, contact with steam can take place at atmospheric pressure (steaming) or at autogenous pressure (autoclaving). Several combined cycles of thermal or hydrothermal treatments can be carried out. After this treatment or these treatments, the catalyst precursor comprises nickel in oxide form, i.e. in NiO form.

In the case of hydrothermal treatment, the water content is preferably comprised between 150 and 900 grams per kilogram of dry air, and even more preferably between 250 and 650 grams per kilogram of dry air.

Step k) Reduction by a Reducing Gas

Prior to the use of the catalyst in the catalytic reactor and the implementation of a hydrogenation process, at least one reducing treatment step k) is advantageously carried out in the presence of a reducing gas after steps i) or j) so as to obtain a catalyst comprising nickel at least partially in metallic form.

This treatment makes it possible to activate said catalyst and to form metal particles, in particular of nickel in the zero-valent state. Said reducing treatment can be carried out in-situ or ex-situ i.e. after or before the loading of the catalyst into the hydrogenation reactor. Said reducing treatment step k) can be implemented on the catalyst before being subjected, or not subjected, to passivation step I) described below.

The reducing gas is preferably hydrogen. The hydrogen can be used pure or in a mixture (for example a hydrogen/nitrogen, hydrogen/argon, hydrogen/methane mixture). In the case where the hydrogen is used in a mixture, all proportions can be envisaged.

Said reducing treatment is carried out at a temperature comprised 120 and 500° C., preferably between 150 and 450° C. When the catalyst does not undergo passivation, or undergoes a reducing treatment before passivation, the reducing treatment is carried out at a temperature comprised between 350 and 500° C., preferably between 350 and 450° C. When the catalyst has undergone passivation beforehand, the reducing treatment is generally carried out at a temperature comprised between 120 and 350° C., preferably between 150 and 350° C.

The duration of the reducing treatment is generally comprised between 2 and 40 hours, preferably between 3 and 30 hours. The rise in temperature up to the desired reducing temperature is generally slow, for example fixed between 0.1 and 10° C./min, preferably between 0.3 and 7° C./min.

The hydrogen flow rate, expressed in L/hour/gram of catalyst is comprised between 0.1 and 100 L/hour/gram of catalyst, preferably between 0.5 and 10 L/hour/gram of catalyst, even more preferably between 0.7 and 5 L/hour/gram of catalyst.

Step I) Passivation

Prior to its utilization in the catalytic reactor, the catalyst according to the invention can optionally undergo a step of passivation (step I) with a sulphur- or oxygen-containing compound, or with $CO_2$ before or after reducing treatment step k). This passivation step can be carried out ex-situ or in-situ. The passivation step is carried out by implementation of the methods known to a person skilled in the art.

The step of passivation with sulphur makes it possible to improve the selectivity of the catalysts and to avoid thermal runaways during start up of fresh catalysts. Passivation generally consists of irreversibly poisoning, with the sulphur-containing compound, the most virulent active sites of the nickel which exist on the fresh catalyst and therefore of reducing the activity of the catalyst in favour of its selectivity. The passivation step is carried out by implementation of the methods known to a person skilled in the art, by way of example by the implementation of one of the methods described in patent documents EP0466567, U.S. Pat. No. 5,153,163, FR2676184, WO2004/098774 and EP0707890. The compound is for example selected from the following compounds: thiophene, thiophane, alkyl monosulphides such as dimethyl sulphide, diethyl sulphide, dipropyl sulphide and propyl methyl sulphide or also an organic disulphide of formula HO—$R_1$—S—S—$R_2$—OH such as di-thio-di-ethanol of formula HO—$C_2H_4$—S—S—$C_2H_4$—OH (often called DEODS). The sulphur content is generally comprised between 0.1 and 2% by weight of said element with respect to the mass of the catalyst.

The passivation step with an oxygen-containing compound or with $CO_2$ is generally carried out after a prior reducing treatment at high temperature, generally comprised between 350 and 500° C., and makes it possible to preserve the metallic phase of the catalyst in the presence of air. A second reducing treatment at a lower temperature generally between 120 and 350° C., is then generally carried out. The oxygen-containing compound is generally air or any other flow containing oxygen.

Selective Hydrogenation Process

The present invention also relates to the use of the catalyst according to the invention in a hydrogenation process and in particular in a process for the selective hydrogenation of polyunsaturated compounds such as the diolefins, acetylenics or alkenylaromatics, also called styrenics.

The mono-unsaturated organic compounds such as for example ethylene and propylene, are at the source of the manufacture of polymers, plastics and other chemicals with added value. These compounds are obtained from natural gas, naphtha or gasoil which have been treated by steam cracking or catalytic cracking processes. These processes are carried out at high temperature and produce, in addition to the sought monounsaturated compounds, polyunsaturated organic compounds such as acetylene, propadiene and methyl acetylene (or propyne), 1,2-butadiene and 1,3-butadiene, vinyl acetylene and ethyl acetylene, and other polyunsaturated compounds, the boiling point of which corresponds to the C5+ gasoline fraction (gasolines containing hydrocarbon-containing compounds having 5 or more carbon atoms), in particular diolefinic or styrenic or indenic compounds. These polyunsaturated compounds are very reactive and lead to parasitic reactions in the polymerization units. It is therefore necessary to eliminate them before upgrading these cuts.

Selective hydrogenation is the main treatment developed in order to specifically eliminate the undesirable polyunsaturated compounds from these hydrocarbon feedstocks. It allows the conversion of the polyunsaturated compounds to the corresponding alkenes or aromatics avoiding complete saturation thereof and therefore the formation of the corresponding alkanes or naphthenes. In the case of steam cracking gasolines used as feedstock, selective hydrogenation also makes it possible to selectively hydrogenate the alkenyl aromatics to aromatics by avoiding the hydrogenation of the aromatic rings.

The feedstock of hydrocarbons treated in the selective hydrogenation process has a final boiling point less than or equal to 250° C. and contains at least 2 carbon atoms per molecule and comprises at least one polyunsaturated compound. By "polyunsaturated compounds" is meant compounds comprising at least one acetylenic function and/or at least one dienic function and/or at least one alkenyl aromatic function.

More particularly, the feedstock is selected from the group constituted by a C2 steam cracking cut, a C3 steam cracking cut, a C4 steam cracking cut, a C5 steam cracking cut and a steam cracking gasoline also called pyrolysis gasoline. The steam cracking gasoline or pyrolysis gasoline corresponds to a hydrocarbon-containing cut, the boiling temperature of which is generally comprised between 0 and 250° C., preferably between 10 and 220° C. The polyunsaturated hydrocarbons to be hydrogenated present in said steam cracking gasoline are in particular diolefinic compounds (butadiene, isoprene, cyclopentadiene etc.), styrenic compounds (styrene, alpha-methylstyrene etc.) and indenic compounds (indene etc.). The steam cracking gasoline generally comprises the C5-C12 cut with traces of C3, C4, C13, C14, C15 (for example between 0.1 and 3% by weight for each of these cuts). For example, a feedstock formed by pyrolysis gasoline generally has the following composition: 5 to 25% by weight of paraffins, 40 to 70% by weight of aromatic compounds, 5 to 20% by weight of mono-olefins, 5 to 40% by weight of diolefins, 1 to 10% by weight of alkenyl aromatic compounds and from 20 to 300 ppm by weight of sulphur, all of the compounds forming 100%. Preferably, the polyunsaturated hydrocarbon feedstock treated according to the selective hydrogenation process according to the invention is a steam cracking gasoline.

The selective hydrogenation process according to the invention is intended to eliminate said polyunsaturated hydrocarbons present in said feedstock to be hydrogenated without hydrogenating the monounsaturated hydrocarbons.

For example, when said feedstock is a C2 cut, the selective hydrogenation process is intended to selectively hydrogenate acetylene. When said feedstock is a C3 cut, the selective hydrogenation process is intended to selectively hydrogenate propadiene and methyl acetate. In the case of a C4 cut, it is intended to eliminate butadiene, vinyl acetylene (VAC) and butyl, in the case of a C5 cut, it is intended to eliminate the pentadienes. When said feedstock is a steam cracking gasoline, the selective hydrogenation process is intended to selectively hydrogenate said polyunsaturated hydrocarbons present in said feedstock to be treated so that the diolefinic compounds are partially hydrogenated to mono-olefins and the styrenic and indenic compounds are partially hydrogenated to corresponding aromatic compounds by avoiding the hydrogenation of the aromatic rings.

The technological implementation of the selective hydrogenation process is for example carried out by injection, with an ascending or descending flow, of the polyunsaturated hydrocarbon feedstock and of the hydrogen into at least one fixed-bed reactor. Said reactor can be of the isothermal type or adiabatic type. An adiabatic reactor is preferred. The polyunsaturated hydrocarbon feedstock can advantageously be diluted with one or more re-injection(s) of the effluent, originating from said reactor where the selective hydrogenation reaction is produced, at various points of the reactor, situated between the inlet and the outlet of the reactor in order to limit the temperature gradient in the reactor. The technological implementation of the selective hydrogenation process according to the invention can also be advantageously carried out by the positioning of at least said catalyst supported in a reactive distillation column or in reactor-exchangers. The flow of hydrogen can be introduced at the same time as the feedstock to be hydrogenated and/or at one or more different points of the reactor.

The selective hydrogenation of the C2, C3, C4, C5 and C5+ cuts can be carried out in gas phase or in liquid phase, preferably in liquid phase for the C3, C4, C5 and C5+ cuts. In fact, a reaction in liquid phase makes it possible to reduce the energy cost and increase the cycle time of the catalyst.

Generally, the selective hydrogenation is carried out at a temperature comprised between 0 and 500° C., at a pressure comprised between 0.1 and 20 MPa, at a hydrogen/(polyunsaturated compounds to be hydrogenated) molar ratio between 0.1 and 10 at an hourly space velocity HSV (defined as the ratio of the volume flow rate of feedstock to the volume of catalyst) comprised between 0.1 and 200 $h^{-1}$ for a liquid feedstock, between 100 and 15,000 $h^{-1}$ for a gaseous feedstock, of a hydrocarbon feedstock containing polyunsaturated compounds containing at least 2 carbon atoms per molecule and having a final boiling point less than or equal to 250° C.

Preferably, a selective hydrogenation process is carried out, in which the feedstock is a steam cracking gasoline comprising polyunsaturated compounds, the (hydrogen)/(polyunsaturated to be hydrogenated) molar ratio is generally comprised between 1 and 2, the temperature is generally comprised between 40 and 200° C., preferably between 50 and 180° C., the hourly space velocity (HSV) is generally comprised between 0.5 and 50 $h^{-1}$, preferably between 1 and 20 $h^{-1}$ and the pressure is generally comprised between 0.3 and 6.5 MPa, preferably between 2.0 and 3.5 MPa. The hydrogen flow rate is adjusted in order to have a sufficient quantity in order to theoretically hydrogenate all of the polyunsaturated compounds and to maintain an excess of hydrogen at the outlet of the reactor.

Process for the Hydrogenation of Aromatics

The present invention also relates to the use of the catalyst according to the invention in a hydrogenation process and in particular in a process for the hydrogenation of aromatics making it possible to transform the aromatic compounds of the petroleum or petrochemical cuts by conversion of the aromatic rings to naphthenic rings.

The feedstock of hydrocarbons treated in the hydrogenation process of the aromatics has a final boiling point less than or equal to 650° C. generally between 20 and 650° C., and preferably between 20 and 450° C., and contains at least one aromatic or polyaromatic compound. As this petroleum or petrochemical cut containing aromatic compounds, kerosene, light gasoil, heavy gasoil and cracking distillates, such as FCC rerun oil, the gasoil from a coking unit, hydrocracking distillates, and reformate from catalytic reforming, may be mentioned by way of example.

The content of aromatic hydrocarbons in a feedstock treated in the hydrogenation process is generally comprised between 0.1 and 80% by weight, preferably between 1 and 50% by weight, and particularly preferably between 2 and 35% by weight, the percentage by weight being based on the total weight of the hydrocarbon feedstock. The aromatics present are for example benzene or alkyl aromatics such as toluene, ethylbenzene, o-xylene, m-xylene, or p-xylene, or also aromatics having several aromatic rings (polyaromatics) such as naphthalene.

The sulphur or chlorine content of the feedstock is generally less than 5000 ppm by weight of sulphur or chlorine respectively, preferably less than 100 ppm by weight, and particularly preferably less than 10 ppm.

The technological implementation of the hydrogenation process of the aromatics can be carried out as described in the selective hydrogenation part.

The hydrogenation of the aromatics can be carried out in gas phase or in liquid phase, preferably in liquid phase. Generally, the hydrogenation of the aromatics is carried out at a temperature comprised between 30 and 350° C., preferably between 50 and 325° C., at a pressure comprised between 0.1 and 20 MPa, preferably between 0.5 and 10 MPa, at a hydrogen/(aromatic compounds to be hydrogenated) molar ratio between 0.1 and 10 and at an hourly space velocity HSV comprised between 0.05 and 50 $h^{-1}$, preferably between 0.1 and 10 $h^{-1}$, of a hydrocarbon feedstock containing aromatic compounds and having a final boiling point less than or equal to 650° C.

The hydrogen flow rate is adjusted in order to have a sufficient quantity in order to theoretically hydrogenate all of the polyunsaturated compounds and to maintain an excess of hydrogen at the outlet of the reactor.

The conversion of the aromatic or polyaromatic compounds is generally greater than 20 mol. %, preferably greater than 40 mol. %, more preferably greater than 80 mol. %, and particularly preferably greater than 90 mol. % of the aromatic or polyaromatic compounds contained in the hydrocarbon-containing feedstock. The conversion is calculated by dividing the difference between the total moles of the aromatic or polyaromatic compounds in the hydrocarbon feedstock and in the product by the total moles of the aromatic or polyaromatic compounds in the hydrocarbon feedstock.

According to a particular variant the catalyst according to the invention is used in a hydrogenation process of a hydrocarbon feedstock containing benzene such as for example the reformate originating from a catalytic reforming unit. The benzene content is generally comprised between 0.1 and 40% by weight, preferably between 0.5 and 35% by weight, and particularly preferably between 2 and 30% by weight, the percentage by weight being based on the total weight of the hydrocarbon feedstock. The sulphur or chlorine content of the feedstock is generally less than 10 ppm by weight of sulphur or chlorine respectively, and preferably less than 2 ppm by weight.

The hydrogenation of the feedstock containing benzene can be carried out in gas phase or in liquid phase, preferably in liquid phase. When it is carried out in liquid phase, a solvent can be present. Generally, the hydrogenation of the benzene is carried out at a temperature comprised between 30 and 250° C., preferably between 50 and 200° C., and more preferably between 80 and 180° C., at a pressure comprised between 0.1 and 10 MPa, preferably between 0.5 and 4 MPa, at a hydrogen/(benzene) molar ratio between 0.1 and 10 and at an hourly space velocity HSV comprised between 0.05 and 50 $h^{-1}$, preferably between 0.5 and 10 $h^{-1}$.

The conversion of the benzene is generally greater than 50 mol. %, preferably greater than 80 mol. %, more preferably greater than 90 mol. %, and particularly preferably greater than 98 mol. %.

The invention is illustrated by the following examples.

EXAMPLES

Example 1: Preparation of an Aqueous Solution of Ni Precursors

The aqueous solution of Ni precursors (solution S) used for the preparation of catalysts A, B and C is prepared by dissolving 46.1 g of nickel nitrate ($NiNO_3$, supplier Strem Chemicals®) in a volume of 13 mL of distilled water. The solution S is obtained, the NiO concentration of which is 20.1% by weight (with respect to the mass of the solution).

Example 2: Preparation of a Catalyst A, According to the Invention

Catalyst A according to the invention is prepared by dry impregnation of the solution S of Ni precursors on an alumina A1. A nickel content of 20% by weight is sought, with respect to the total mass of the catalyst.

The synthesis of the alumina A1 according to the invention is carried out in a 5-liter reactor in seven steps, named a) to g) below. The concentrations of the acid and basic alumina precursors are as follows: aluminium sulphate $Al_2(SO_4)_3$ at 102 g/l as $Al_2O_3$ and sodium aluminate NaAlOO at 155 g/l as $Al_2O_3$. It is sought to obtain a final alumina concentration of 45 g/L in the suspension obtained at the end of second precipitation step c).

a) A first precipitation of aluminium sulphate $Al_2(SO_4)_3$ and sodium aluminate NaAlOO at 30° C. over 8 minutes, pH=9.1 and with a degree of progression of 10%.

This degree of progression corresponds to the proportion of alumina formed as $Al_2O_3$ equivalent during this first step.

b) A temperature rise from 30 to 70° C. over 20 to 30 minutes;

a) A second precipitation of aluminium sulphate $Al_2(SO_4)_3$ and sodium aluminate NaAlOO at 70° C. over 30 minutes, pH=9.1 and with a degree of progression of 90%. This degree of progression corresponds to the proportion of alumina formed as $Al_2O_3$ equivalent during this second precipitation step.

d) Filtration of the suspension obtained at the end of step c) by displacement on a device of the Buchner P4 frit type followed by three successive washings with 5 L of distilled water;

e) Drying the alumina gel overnight at 120° C.

f) The dried alumina gel originating from step e) is formed using a mixer of the "Brabender" type with an acid level of 3% (total acid level, expressed with respect to the dry alumina), a degree of neutralization of 200% and acidic and basic losses on ignition of 62% and 64% respectively. Then extrusion is carried out on a ram extruder through a trilobed die of average diameter 2.1 mm. After extrusion, the extrudates are dried overnight at 80° C.

g) The extrudates obtained at the end of step f) are then calcined at 750° C. under a flow of air of 1 L/h/g of alumina at 750° C. over 2 hours (temperature gradient of 5° C./min). Alumina A1 is obtained.

The characteristics of alumina A1 thus obtained are presented in Table 1 below. Alumina A1 contains no pores with a diameter comprised between 2 and 7 nm.

TABLE 1

Properties of aluminas A1 (according to the invention), and B1 and C1 (comparative)

| | ALUMINAS | | |
|---|---|---|---|
| | A1 According to the invention | B1 Comparative | C1 Comparative |
| BET surface area ($m^2/g$) | 156 | 269 | 298 |
| Total pore volume (mL/g) | 0.85 | 0.64 | 0.60 |
| Mesopore volume (mL/g) | 0.83 | 0.61 | 0.57 |
| Median mesopore volume (nm) | 21 | 9.4 | 17 |
| Macropore volume (mL/g) | 0.02 | 0.03 | 0.03 |
| Macropore volume (% of the total pore volume) | 2 | 5 | 5 |
| Macropore volume (mL/g) | 0 | 0 | 0 |

Catalyst A is then prepared by dry impregnation of the solution S of Ni precursors, described in Example 1, on alumina A1, according to the three steps named h) to i) below.

h) A dry impregnation of alumina A1 by adding dropwise a volume of 11.5 mL of solution S onto a mass of 10.5 g of alumina A1, for a duration of 10 minutes.

i) A drying of the catalytic precursor obtained at the end of step h) in a stove at 120° C. overnight.

j) A heat treatment by calcination of the catalyst dried under a flow of air of 1 L/h/g of catalyst at 450° C. for 2 hours (temperature gradient 5° C./min). Calcined catalyst A is then obtained.

The characteristics of calcined catalyst A thus obtained are presented in Table 2 below. Calcined alumina A contains no pores with a diameter comprised between 2 and 7 nm.

TABLE 2

Properties of catalysts A (according to the invention), and B and C (comparative)

| | CATALYSTS | | |
|---|---|---|---|
| | A According to the invention | B Comparative | C Comparative |
| Ni (% by weight) | 20.3 | 21.5 | 21.0 |
| BET surface area ($m^2/g$) | 117 | 188 | 206 |
| Total pore volume (mL/g) | 0.64 | 0.44 | 0.43 |
| Mesopore volume (mL/g) | 0.62 | 0.41 | 0.40 |
| Median mesopore volume (nm) | 19 | 9 | 16 |
| Macropore volume (mL/g) | 0.02 | 0.03 | 0.03 |
| Macropore volume (% of the total pore volume) | 3 | 7 | 7 |
| Macropore volume (mL/g) | 0 | 0 | 0 |
| Size of the NiO crystallites (nm) | 15.2 | 14.1 | 11.0 |

Example 3: Preparation of Catalyst B Having a Different Pore Distribution (Comparative)

Catalyst B is prepared by dry impregnation of the solution S of Ni precursors aiming at a content of 20% by weight of nickel with respect to the total mass of the catalyst on an alumina B1 having a pore distribution different from that of alumina A1 described in Example 2 above. The characteristics of this alumina B1 are presented in Table 1. In particular, this alumina B1 has a mesopore median diameter very much less than that of alumina A1 as well as a total pore volume and a mesopore volume less than those of alumina A1.

Catalyst B is then prepared by dry impregnation of the solution S of Ni precursors, described in Example 1, on alumina B1. On this alumina with a low pore volume, two successive impregnations were necessary to reach an Ni content of approximately 20% by weight; the sequence of the three steps h) to i) of Example 2 described above, was then repeated twice (according to the sequence h, i, j, h, i, j). The first impregnation step makes it possible to obtain a content of 14.9% by weight of nickel, the second impregnation step makes it possible to achieve a content of 21.5% by weight of nickel, with respect to the total mass of the catalyst. For each step, the operating conditions are strictly identical to those described in Example 2 above. Calcined catalyst B is then obtained.

The characteristics of calcined catalyst B thus obtained are presented in Table 2. It shows a mesopore median diameter very much less than that of catalyst A as well as a total pore volume, a mesopore volume and crystallites of NiO smaller than those of catalyst A.

Example 4: Preparation of Catalyst C Having a Different Pore Distribution (Comparative)

Catalyst C is prepared by dry impregnation of the solution S of Ni precursors aiming at a content of 20% by weight of nickel with respect to the total mass of the catalyst on an alumina C1 having a pore distribution also different from that of alumina A1 described in Example 2 above. The characteristics of this alumina C1 are presented in Table 1. In particular, this alumina C1 has a total pore volume and a mesopore volume less than those of alumina A1 but a median mesopore volume close to that of alumina A1.

Catalyst C is then prepared by dry impregnation of the solution S of Ni precursors, described in Example 1, on alumina C1. On this alumina with a low pore volume, two successive impregnations were necessary to reach an Ni content of approximately 20% by weight; the sequence of the three steps h) to i) of Example 2 described above, was then repeated twice (according to the sequence h, i, j, h, i, j). The first impregnation step makes it possible to obtain a content of 13.3% by weight of nickel, the second impregnation step makes it possible to achieve a content of 21.0% by weight of nickel, with respect to the total mass of the catalyst. For each step, the operating conditions are strictly identical to those described in Example 2 above. Calcined catalyst C is then obtained.

The characteristics of calcined catalyst C thus obtained are presented in Table 2 below. It shows a total pore volume and a mesopore volume and crystallites of NiO smaller than those of catalyst A.

Example 5: Evaluation of the Catalytic Properties of Catalysts A, B and C in Selective Hydrogenation of a Mixture Containing Styrene and Isoprene Catalysts A, B and C described in the above examples are tested vis-à-vis the selective hydrogenation reaction of a mixture containing styrene and isoprene.

The composition of the feedstock to be selectively hydrogenated is as follows: 8% by weight of styrene (supplier Sigma Aldrich®, purity 99%), 8% by weight of isoprene (supplier Sigma Aldrich®, purity 99%), 84% by weight of n-heptane (solvent) (supplier VWR®, purity>99% chromanorm for HPLC). This feedstock also contains sulphur-containing compounds in a very low quantity: 10 ppm by weight of sulphur introduced in the form of pentanethiol (supplier Fluka®, purity>97%) and 100 ppm by weight of sulphur introduced in the form of thiophene (supplier Merck®, purity 99%). This composition corresponds to the initial composition of the reaction medium. This mixture of model molecules is representative of a pyrolysis gasoline.

The selective hydrogenation reaction is carried out in a stainless steel 500 mL autoclave equipped with a magnetically driven mechanical stirrer and being able to operate under a maximum pressure of 100 bar (10 MPa) and at temperatures comprised between 5° C. and 200° C.

Prior to its introduction into the autoclave, a quantity of 3 mL of catalyst is reduced ex situ under a flow of hydrogen of 1 L/h/g of catalyst, at 400° C. for 16 hours (temperature gradient 1° C./min); it is then transferred into the autoclave, with exclusion of air. After the addition of 214 mL of n-heptane (supplier VWR®, purity>99% chromanorm for HPLC), the autoclave is closed, purged, then pressurized under 35 bar (3.5 MPa) of hydrogen, and heated to the test temperature equal to 30° C. At time t=0, approximately 30 g of a mixture containing styrene, isoprene, n-heptane, pentanethiol and thiophene is introduced into the autoclave. The reaction mixture then has the composition described above and stirring is started at 1600 rpm. The pressure is kept constant at 35 bar (3.5 MPa) in the autoclave using a reservoir bottle situated upstream of the reactor.

The progress of the reaction is monitored by taking samples of the reaction medium at regular time intervals: the styrene is hydrogenated to ethylbenzene, without hydrogenation of the aromatic ring, and the isoprene is hydrogenated to methyl-butenes. If the reaction is continued longer than necessary, the methyl-butenes are in turn hydrogenated to isopentane. The hydrogen consumption is also monitored over time by the reduction of pressure in a reservoir bottle situated upstream of the reactor. The catalytic activity is expressed in moles of $H_2$ consumed per minute and per gram of Ni.

The catalytic activities measured for catalysts A, B and C are presented in Table 3 below. They are related to the catalytic activity measured for catalyst A ($A_{HYD1}$).

TABLE 3

Comparison of the selective hydrogenation performances of a mixture containing styrene and isoprene ($A_{HYD1}$) and hydrogenation of toluene ($A_{HYD2}$).

| Catalyst | According to the invention? | Size of the NiO crystallites (nm) | $A_{HYD1}$ (%) | $A_{HYD2}$ (%) |
|---|---|---|---|---|
| A | Yes | 15.2 | 100 | 100 |
| B | No | 14.1 | 48 | 41 |
| C | No | 11.0 | 63 | 54 |

This clearly shows the improved performances of catalyst A prepared according to the invention and in particular the impact of its specific textural properties. In fact, although they have NiO crystallites smaller than those of catalyst A, catalysts B and C have poorer catalytic performances. The presence of mesopores of a controlled size is therefore necessary in order to obtain the improved performances of catalyst A.

Example 6: Evaluation of the Catalytic Properties of Catalysts a, B and C in Hydrogenation of Toluene Catalysts A, B and C described in the above examples are also tested vis-à-vis the hydrogenation reaction of toluene.

The selective hydrogenation reaction is carried out in the same autoclave as that described in Example 5.

Prior to its introduction into the autoclave, a quantity of 2 mL of catalyst is reduced ex situ under a flow of hydrogen of 1 L/h/g of catalyst, at 400° C. for 16 hours (temperature gradient 1° C./min); it is then transferred into the autoclave, with exclusion of air. After the addition of 216 mL of n-heptane (supplier VWR®, purity>99% chromanorm for HPLC), the autoclave is closed, purged, then pressurized under 35 bar (3.5 MPa) of hydrogen, and heated to the test temperature equal to 80° C. At time t=0, approximately 26 g of toluene (supplier SDS®, purity>99.8%) is introduced into the autoclave (the initial composition of the reaction mixture is then toluene 6% by weight/n-heptane 94% by weight) and stirring is started at 1600 rpm.

The pressure is kept constant at 35 bar (3.5 MPa) in the autoclave using a reservoir bottle situated upstream of the reactor.

The progress of the reaction is monitored by taking samples of the reaction medium at regular time intervals: the toluene is completely hydrogenated to methylcyclohexane. The hydrogen consumption is also monitored over time by the reduction of pressure in a reservoir bottle situated upstream of the reactor. The catalytic activity is expressed in moles of $H_2$ consumed per minute and per gram of Ni.

The catalytic activities measured for catalysts A, B and C are presented in Table 3. They are related to the catalytic activity measured for the catalyst A ($A_{HYD2}$). The improved performances of catalyst A prepared according to the invention are shown.

The invention claimed is:

1. A supported catalyst comprising a calcined, predominantly aluminium, oxide support and an active phase comprising nickel, the nickel content being 5 to 65% by weight of said element with respect to the total mass of the catalyst, said active phase comprising no group VIB metal, the nickel particles having a diameter less than or equal to 20 nm, said catalyst having a mesopore median diameter greater than or equal to 14 nm, a mesopore volume measured by mercury porosimetry greater than or equal to 0.45 mL/g, a total pore volume measured by mercury porosimetry greater than or equal to 0.45 mL/g, a macropore volume less than 3.5% of the total pore volume, said catalyst being in the form of grains having an average diameter comprised between 0.5 and 10 mm.

2. The catalyst according to claim 1, in which the mesopore median diameter of the catalyst is comprised between 18 and 25 nm.

3. The catalyst Catalysts according to claim 1, in which the mesopore volume of the catalyst is 0.55 ml/g to 0.95 ml/g.

4. The catalyst according to claim 1, in which the nickel content is 10 to 34% by weight of said element with respect to the total mass of the catalyst.

5. The catalyst according to claim 1, containing no pores with a diameter between 2 and 7 nm.

6. The catalyst according to claim 1, containing no micropores.

7. A process for the preparation of a catalyst according to claim 1 comprising:
   a) precipitating, in an aqueous reaction medium, at least one basic precursor that is sodium aluminate, potassium aluminate, ammonium hydroxide, sodium hydroxide or potassium hydroxide and at least one acidic precursor that is aluminium sulphate, aluminium chloride, aluminium nitrate, sulphuric acid, hydrochloric acid or nitric acid, in which at least one of the basic or acidic precursors comprises aluminium, the relative flow rate of the acidic and basic precursors is selected so as to obtain a pH of the reaction medium of 8.5 to 10.5 and the flow rate of the acidic and basic precursor(s) containing aluminium is adjusted so as to obtain a degree of progression in (a) of 5 to 13%, the degree of progression being defined as the proportion of alumina formed in $Al_2O_3$ equivalent during said precipitation in (a) with respect to the total quantity of alumina formed in $Al_2O_3$ equivalent at the end of (c) of the preparation process, said precipitation (a) taking place at a temperature of 20 to 90° C. and for a duration of 2 to 30 minutes;
   b) heating the suspension obtained in (a) at a temperature of 40 to 90° C. for a duration of 7 to 45 minutes in order to obtain an alumina gel,
   c) a second precipitation of the suspension obtained at the end of heating b) by adding, to the suspension, at least one basic precursor that is sodium aluminate, potassium aluminate, ammonium hydroxide, sodium hydroxide or potassium hydroxide and at least one acidic precursor that is aluminium sulphate, aluminium chloride, aluminium nitrate, sulphuric acid, hydrochloric acid or nitric acid, in which at least one of the basic or acidic precursors comprises aluminium, the relative flow rate of the acidic and basic precursors is selected so as to obtain a pH of the reaction medium of 8.5 to 10.5 and the flow rate of the acidic and basic precursor(s) containing aluminium is adjusted so as to obtain a degree of progression of the second precipitation of 87 to 95%, the degree of progression being defined as the proportion of alumina formed in $Al_2O_3$ equivalent during said second precipitation with respect to the total quantity of alumina formed in $Al_2O_3$ equivalent at the end of c) of the preparation process, said precipitation taking place at a temperature of 40 to 90° C. and for a duration of 2 to 50 minutes;
   d) filtration of a suspension obtained at the end of the second precipitation c) in order to obtain an alumina gel,
   e) drying said alumina gel obtained in d) in order to obtain a powder,
   f) forming the powder obtained at the end of e) in order to obtain a crude material,
   g) heat treating the crude material obtained at the end of f) at a temperature of 500 to 1000° C., in the presence or absence of an air flow containing up to 60% by volume of water, in order to obtain a calcined aluminium oxide support;
   h) impregnating said support with a solution comprising the salt(s) of the precursor(s) of the nickel-based active phase;
   i) drying said impregnated support at a temperature of 15 to 250° C. so as to obtain a dried catalyst,
   j) optionally heat treating said dried catalyst at a temperature of 250 to 1000° C., in the presence or absence of water.

8. The process according to claim 7, in which at least one reducing treatment k) is carried out in the presence of a reducing gas after i) or j) so as to obtain a catalyst comprising nickel at least partially in metallic form.

9. The process according to claim 8, in which passivation l) is carried out with a sulphur- or oxygen-containing compound, or with $CO_2$ before or after reducing treatment k).

10. The process according to claim 7, in which the degree of progression of the first precipitation a) is 6 to 12%.

11. The process according to claim 7, in which the acidic precursor of a) and c) is aluminium sulphate, aluminium chloride or aluminium nitrate, and in which the basic precursor of a) and c) is sodium aluminate or potassium aluminate.

12. A hydrogenation process comprising contacting the catalyst according to claim 1, in the presence of hydrogen, with a feedstock of hydrocarbons containing polyunsaturated and/or aromatic compounds so as to obtain an at least partially hydrogenated effluent.

13. The hydrogenation process according to claim 12 comprising selective hydrogenation of a hydrocarbon feedstock containing polyunsaturated compounds containing at least 2 carbon atoms per molecule and having a final boiling point less than or equal to 250° C. at a temperature of 0 to 500° C., at a pressure 0.1 to 20 MPa, at a hydrogen/(polyunsaturated compounds to be hydrogenated) molar ratio of 0.1 to 10 at an hourly space velocity HSV of 0.1 to 200 $h^{-1}$ for a liquid feedstock, 100 to 15,000 $h^{-1}$ for a gaseous feedstock.

14. The hydrogenation process according to claim 12 in which a hydrogenation of the aromatics is carried out at a temperature of 30 to 350° C., at a pressure of 0.1 to 20 MPa, at a hydrogen/(aromatic compounds to be hydrogenated) molar ratio between 0.1 and 10 and at an hourly space velocity HSV of 0.05 to 50 $h^{-1}$, said hydrocarbon feedstock containing aromatic compounds and having a final boiling point less than or equal to 650° C.

* * * * *